United States Patent [19]
Hoepp et al.

[11] Patent Number: 5,216,179
[45] Date of Patent: Jun. 1, 1993

[54] METHOD OF PRODUCING MIXTURES OF CYCLIC ACROLEIN GLYCEROL ACETALS

[75] Inventors: Mathias Hoepp, Biebergemuend; Dietrich Arntz, Oberursel; Stephan Bartsch, Freigericht-Somborn; Adolf Schaefer-Sindlinger, Frankfurt am Main; Wolfgang Boeck, Langenselbold, all of Fed. Rep. of Germany

[73] Assignee: Degussa Aktiengesellschaft, Frankfurt am Main, Fed. Rep. of Germany

[21] Appl. No.: 801,930

[22] Filed: Dec. 3, 1991

[30] Foreign Application Priority Data

Dec. 17, 1990 [DE] Fed. Rep. of Germany ....... 4040362

[51] Int. Cl.$^5$ .................. C07D 319/06; C07D 317/20
[52] U.S. Cl. ..................................... 549/372; 549/453
[58] Field of Search ............................... 549/372, 453

[56] References Cited

U.S. PATENT DOCUMENTS 3,014,924 12/1961 Brachman .
3,250,788 5/1966 Kiff et al. .
4,003,918 1/1977 Hughes .

*Primary Examiner*—Nicky Chan
*Attorney, Agent, or Firm*—Beveridge, DeGrandi, Weilacher & Young

[57] ABSTRACT

Mixed cyclic acrolein glycerol acetals can be obtained by reacting acrolein with glycerol in the presence of a solid acidic catalyst and by a distillation workup in a higher space-time yield and in very high selectivity in comparison to the state of the art if the reaction is carried out in the presence of the reaction mixture as solvent, which mixture consists essentially of acrolein, glycerol, cyclic acrolein glycerol acetals and water, and in the absence of heterogeneous solvents and, to the extent necessary, the reaction mixture freed of catalyst is compounded prior to being worked up by distillation with such an amount of pH-increasing substance that it exhibits a pH in a range of 4.5 to 7 in tenfold dilution with water. The reaction preferably takes place at 10° to 30° C. using strongly acidic organic or inorganic ion exchangers.

12 Claims, No Drawings

METHOD OF PRODUCING MIXTURES OF CYCLIC ACROLEIN GLYCEROL ACETALS

BACKGROUND OF THE INVENTION

The present invention relates to a method of producing mixtures of cyclic acrolein glycerol acetals. More particularly, the present invention relates to a method for producing mixtures of cis-2-vinyl-4-hydroxymethyl-1,3-dioxolane, trans-2-vinyl-4-hydroxymethyl-1,3-dioxolane, cis-2-vinyl-5-hydroxy-1,3-dioxane and trans-2-vinyl-5-hydroxy-1,3-dioxane. The method is based on the acid-catalyzed reaction of acrolein with glycerol and is especially suited for the continuous production of mixtures of cyclic acrolein glycerol acetals.

The production of cyclic acetals of acrolein with glycerol by means of reacting acrolein and glycerol in the presence of a solid acid catalyst is known; see U.S. Pat. No. 3,014,924 and J. Org. Chem. (1960), pp. 319-324. Highly porous carrier materials coated with mineral acids such as silica, silica gel, and silicoaluminates serve as catalyst. The reaction takes place at temperatures between 50° and 150° C., especially 100° and 125° C., during which the reaction water is distilled of in an azeotropic manner by means of an organic solvent such as benzene, toluene, chloroform or cyclohexane. A disadvantage of this method is the low space-time yield, which can be traced, among other reasons, to the fact that the main amount of the glycerol is at first present as a separate phase. The high reaction temperature required when using a small amount of catalyst entails the danger, in conjunction with the long reaction time, of the formation of byproducts. An elevated amount of catalyst does accelerate the acetal formation but at the same time byproducts are formed in an amount which can not be tolerated.

As regards a continuous process, the use of acrolein as the azeotrope entrainer is advised against as this favors the formation of byproducts. Finally, the use of a heterogeneous organic solvent increases the engineering expense significantly and reduces the economy. The repetition of the method of U.S. Pat. No. 3,014,924 on an industrial scale, as shown herein below, corroborates the unsatisfactory space-time yield and makes it clear that a continuous method can not be operated in an economic manner on this basis.

It is also known that acrolein can be reacted under homogeneous catalysis with a 1,3-diol using mineral acids or sulfonic acids as catalyst (U.S. Pat. No. 4,108,869). The diol is fed into an extraction column in an excess from above and contains the acid. Acrolein is fed into the middle, which acrolein reacts with the downward-flowing diol. A solvent, such as hexane, is fed in from below in countercurrent flow which solvent mixes poorly with the diol. The hexane phase and the diol-water phase are worked up by distillation. This method can not be transferred to the production of acrolein glycerol acetals because acrolein and glycerol do not mix with one another and therefore an insufficient reaction takes place in the extraction column.

A strongly acidic cation exchanger as catalyst for the reaction of 2-methyl-1,3-propanediol with acrolein is suggested in a comparative example of U.S. Pat. No. 4,108,869. The reaction mixture, which is homogeneous at first, separates into an acetal phase and an aqueous phase. Due to the immiscibility of acrolein with glycerol, the previously described method can not be used for an economical production of the desired cyclic acrolein glycerol acetal mixtures.

SUMMARY OF THE INVENTION

An object of the present invention is to provide a method for the production of mixtures of cyclic acrolein glycerol acetals which does not exhibit the disadvantages of the method known from U.S. Pat. No. 3,014,924. The method should achieve a high space-time yield with high selectivities and be able to be carried out in the absence of heterogeneous solvents. Finally, the method should also be able to be carried out in a continuous and economical manner.

In attaining the above and other objects, a features of the invention resides in a method for the preparation of mixtures of cyclic acrolein glycerol acetals by means of reacting acrolein with glycerol in the presence of a solid, acidic catalyst and by working up the resulting reaction mixture by means of distillation. The method is characterized in that the reaction is carried out in the presence of the reaction mixture as solvent, which mixture consists essentially of acrolein, glycerol, cyclic acrolein glycerol acetals and water, and in the absence of heterogeneous solvents. The resulting reaction mixture is freed of catalyst, and, to the extent necessary, the reaction mixture freed of catalyst is compounded prior to being worked up by distillation with such an amount of pH-increasing substance that it exhibits a pH in a range of 4.5 to 7 when diluted with ten times the amount of water. Distillation then follows.

In a more detailed aspect, the reaction is carried out at a temperature in a ranqe of 0° to 50° C., preferably 10° to 30° C. As catalyst it has been found that strongly acidic organic or inorganic ion exchangers in the H form, especially ion exchangers containing sulfonate groups, can be used. In general, acrolein and glycerol are added in a molar ratio of greater that 1 to 1 to 5 to 1, especially 1.5 to 2.5 to 1.

A further feature of the invention resides in carrying out the method so that a reaction mixture is used as solvent which was obtained from the reaction of acrolein with glycerol in a molar ratio of 1.5 to 2.5 and contains 40 to 50% by weight of cyclic acrolein glycerol acetals.

A buffer solution with a pH in a range of 5 to 7, preferably 5.5 to 6.5, is used as pH-increasing substance. Even more preferably, the reaction mixture is compounded with such an amount of buffer solution that it exhibits a pH in a range of 5.5 to 7 in tenfold dilution with water.

The method of the invention can be carried out in a continuous manner by dosing acrolein and glycerol in the desired molar ratio in a continuous manner into the reaction mixture functioning as solvent, reacting them in the presence of the solid acidic catalyst, continuously removing the amount of reaction mixture corresponding to the amount dosed in and recovering the product.

DETAILED DESCRIPTION OF THE INVENTION

The method of the invention results in a high space-time yield and selectivity of the reaction. The reaction can surprisingly be carried out at low temperatures and without azeotropic removal of water. Thus, it requires neither the expensive use of a heterogeneous solvent nor the selectivity-reducing, azeotropic removal of water by means of acrolein, which is also hazardous for safety reasons.

Since acrolein and glycerol are not miscible with one another, the acrolein glycerol acetal formed functions as solubilizer. The reaction mixture, which is used as a solvent, consists essentially of a mixture of cyclic acrolein glycerol acetals as well as of the reactants acrolein and glycerol and the reaction water. The term "essentially" denotes that the reaction can additionally contain reaction-conditioned byproducts. The composition of the reaction is a function of the molar ratio of acrolein to glycerol selected and of the reaction temperature and preferably corresponds to the particular equilibrium composition. The reaction mixture which is necessary at first for the method of the invention can be produced in any manner desired, e.g. by means of mixing the components. In principle, glycerol and acrolein can also be reacted to the required equilibrium reaction mixture in the absence of a solvent. However, the reaction takes place in this instance in a two-phase system at first and a long reaction time is thus necessary. In order to avoid a two-phase formation during the acetal formation of the invention, the reaction mixture should always contain a sufficient amount of acrolein-glycerol-acetal mixture, preferably 35 to 50 % by weight. The suitable amount of the reaction mixture functioning as solvent as well as the concentration of acrolein glycerol acetals can be readily determined by orientation tests. Given a molar ratio of acrolein to glycerol of 2 to 1 and a reaction temperature of 20° C., the concentration of acrolein glycerol acetals in the reaction mixture should not drop below 36 % by weight.

The molar ratio of acrolein to glycerol is not very critical for the reaction and each of the two initial components can be added in excess. The molar ratio is advantageously a function of the workup of the reaction mixture. Thus, if a pure acetal mixture is to be obtained or a reaction mixture freed of acrolein with low glycerol content is to be used by itself, a molar ratio of acrolein to glycerol of greater than 1 to 1 to 5 to 1 is recommended, but a molar ratio in a range of 1.5 to 1 to 2.5 to 1 is preferred. An excess of acrolein in comparison to glycerol further lowers the viscosity of the reaction mixture. The reactants are added in the desired molar ratio to the reaction mixture functioning as solvent in such a manner and distributed therein so that only one liquid phase is always present in addition to the solid catalytic phase.

The method of the invention can be carried out both at a rather low temperature or also at temperatures up to 100° C. In general, however, use should be made of the advantage of lower temperatures possible in accordance with the invention and the reaction should be carried out at 0° to 50° C., preferably 10° to 30° C. and especially at 10 to 20° C. In the case of a higher temperature, the equilibrium is shifted more to the side of the charging stock and, in addition, byproducts are formed in an increased manner. In the case of very low temperature, the reaction speed may be too low to achieve the high space-time yield striven for, and, in addition, the elevated viscosity of the reaction mixture given at a low temperature can lead to engineering problems, e.g. A high pressure drop if the reaction mixture is pumped over a fixed bed catalyst. The reaction is customarily carried out at normal pressure; to the extent that it is desired or necessary at a higher temperature, an increased pressure can also be adjusted.

Solid, acidic catalysts which are insoluble in the reaction mixture are used as catalyst. In particular, inorganic and organic ion exchangers in the H form can be used, which does not mean that all exchangeable groups must be present in the H form but rather only a purposeful number which can be determined by an orienting test. Strongly acidic ion exchangers are preferred. Inorganic carrier materials with a high surface can also be used which contain a strong mineral acid absorbed in a sufficiently fixed manner—the acid should separate practically not at all from the catalytic surface during the reaction.

Among the organic ion exchangers, exchange resins based on styrene/divinylbenzene copolymers with sulfonate groups or phosphonate groups are especially suitable and those with more strongly acidic sulfonate groups are preferred. It is advantageous to use macroporous ion exchangers. Conventional commercial perfluorinated sulfonic acid resins can also be used. Weakly acidic ion exchangers with carboxyl groups have proved to be hardly effective.

The acidic inorganic ion exchangers preferably include those based on polymeric organosiloxanes with sulfonate groups according to DE patent 35 18 881 and DE patent 32 26 093. Furthermore, acidic zeolites whose $SiO_2/Al_2O_3$ is greater than 2 to 1 such as zeolites of the Y type, mordenite, ZSM 5 and silicalite, as well as layer silicates with acidic intermediary layers, e.g. montmorillonites pretreated with mineral acids can be used.

The method of the invention can be carried out discontinuously, e.g. in an agitator reactor, or continuously, e.g. in a loop reactor, in which the catalyst can be located as a fixed bed or a fluid bed. In principle, all reactor forms are suitable which assure a sufficient contact between the reaction mixture and the solid catalyst. In the continuous method, acrolein and glycerol are continuously fed in the desired molar ratio to the reaction mixture and the corresponding amount of reaction mixture drawn off for workup. The contact time of the reaction mixture, expressed by the LHSV value (liquid hourly space velocity), follows the rule that long residence times on the catalyst yield an increased amount of byproducts but short residence times do not yield sufficient conversion. The LHSV value (liter reaction mixture per liter catalyst (dry) and hour) should be between 1 and 30, preferably between 3 and 20.

In a continuous reaction in an agitated tank reactor, the reaction mixture is agitated together with the catalyst; in a continuous reaction in a loop reactor with a catalytic fixed bed, the reaction mixture is circulated over the bed. In a discontinuous embodiment in an agitated tank, the reactants are added to an amount of reaction mixture in a receiver just fast enough so that no second liquid phase occurs.

The reaction mixture formed in accordance with the invention preferably exhibits a content of 35 to 50% by weight, especially 40 to 50% by weight of cyclic acrolein glycerol acetals and a reaction-conditioned pH in a range of in general 3.0 to 6.0, usually from 3 to 4.5 measured in a tenfold dilution with water. To the extent necessary, a sufficient amount of a substance which increases the pH must be added to the reaction mixture freed of catalyst before the workup by distillation; a pH in a range of 4.5 to 7, preferably 5.5 to 7 and especially 6 to 7, measured in a specimen diluted tenfold with water, should be adjusted. Potential pH-increasing substances are substances with a basic action vis-à-vis the reaction mixture; aqueous buffer solutions with a pH in a range of 5 to 7, especially 5.5 to 6.5, are preferred, e.g.

citrate/NaOH buffer. The elevation of pH is usually necessary as otherwise resplitting of the acetal mixture, catalyzed by the acid formed as byproduct, occurs during the distillation of the acrolein. A pH of above 7 is to be avoided in the reaction mixture as a spontaneous polymerization of the acrolein will otherwise take place. In general, only very small amounts of pH-increasing substances such as buffer solutions are necessary. In as far as the pH of the reaction mixture drawn off from the reactor is around or above 4.5, measured in tenfold dilution, an increase of pH before distillation can optionally be dispensed with.

For the workup, acrolein is first distilled off, then water, then the acrolein glycerol acetals and finally the glycerol. The recovered acrolein and g are returned into the reactor.

It could not have been foreseen that the method would offer the advantages already indicated by means of using the reaction mixture as solvent and by neutralizing acidic byproducts before workup by distillation. The high space-time yield permits an economic and continuous production of the acetal mixture. The low reaction temperature results in a high selectivity and therewith in pure products. The superfluity of a heterogeneous solvent and of an azeotropic distillation results in low technical expense and low production costs.

DETAILED EXAMPLES

Reference example

Example 6 of US 3,014,924 was transferred to a larger scale. 105 kg acrolein, 139 kg glycerol and 300 l toluene were reacted in the presence of 3.5 kg of a precipitated silica coated with 1 % $H_2SO_4$. A reaction time of 9 hours is necessary until a complete separation of water is obtained.

Example 1

A catalytic fixed bed with 4 l Amberlyst 15 (dry) (a strongly acidic ion exchanger of Rohm & Haas) is built into a loop reactor with 40 l total volume. A reaction mixture with the approximate composition of 32% by weight acrolein, 45% by weight acrolein glycerol acetals, 12% by weight glycerol, 8 % by weight water and 3% by weight byproducts is continuously pumped in a circuit at an internal temperature of 15° C. 16.2 kg glycerol/h (176.0 moles) and 19.8 kg acrolein (96%)/h (339.4 moles) are continuously fed in and the corresponding amount of reaction mixture (36 kg/h) drawn off (LHSV =8.2). 2 ml of a 1-normal Na citrate buffer with a pH 6 is continuously fed into the draining reaction mixture per liter. The reaction mixture obtained in this manner is subjected to a fractionated distillation in which 11.53 kg acrolein (96%), 2.88 kg water, 16.20 kg acrolein glycerol acetals and 4.32 kg glycerol are obtained per hour. The recovered acrolein and glycerol are readded. The added acrolein is reacted to 41.7% with a selectivity of 87.7% and the added glycerol is reacted to 73.3 % with a selectivity of 96.5%.

Example 2

91 g acrolein/h and 73 g glycerol/h are continuously fed into a agitated tank reactor charged with 21 g Amberlyst 15 and 320 ml reaction mixture composed of 33.5% acrolein, 11.1% glycerol, 43.9% acrolein glycerol acetal, 8.8% water and 2.7 % byproducts at 15° C. internal temperature. The corresponding amount of reaction mixture (164 g/h) (LHSV=4.2) is continuously removed from the reactor via an overflow and analyzed, during which the composition remains to a large extent constant. The fed-in acrolein is reacted to 39.6% with a selectivity of 89.6%. The fed-in glycerol is reacted to 75% with a selectivity of 93.1%.

Example 3

This example was carried out like example 2 but with an increased internal temperature of 25° C. The reaction mixture obtained is composed of 30.7% acrolein, 9.8% glycerol, 39.2% acrolein glycerol acetals, 8.2% water and 12.1% byproducts. Acrolein is reacted to 44.6% with a selectivity of 70.9% and glycerol to 78 0% with a selectivity of 79.9%.

Example 4

This example was carried out like example 2 but with lower infeed rates and thus increased residence times. 45.3 g acrolein/h and 36.1 g glycerol/h are fed in. The reaction product obtained is composed of 31.5% acrolein, 6.7% glycerol, 43.4% acrolein glycerol acetals, 8.4% water and 10.0% byproducts. Acrolein is reacted to 43.4% with a selectivity of 77.4% and glycerol is reacted to 84.8% with a selectivity of 81.7%.

Example 5

This example was carried out like example 2 but with higher infeed rates and thus lower residence times (LHSV= 16.1). 357.0 g acrolein/h and 264.6 g glycerol/h are fed in. The reaction product obtained is composed of 40.4% acrolein, 14.7% glycerol, 36.3% acrolein glycerol acetals, 7.1% water and 1.5% byproducts. Acrolein is reacted to 29.6% with a selectivity of 91.8% and glycerol is reacted to 65.4% with a selectivity of 92.1%.

Example 6

This example was carried out like example 2 but with a changed molar ratio of acrolein to glycerol of 1 to 1. 66.5 g acrolein/h and 105.0 g glycerol/h are fed in. The reaction product obtained is composed of 14.5% acrolein, 22.1% glycerol, 46.0% acrolein glycerol acetal, 8.8% water and 8.6 % byproducts. Acrolein is reacted to 62.6% with a selectivity of 81.7% and glycerol is reacted to 63.9% with a selectivity of 83.2%.

Example 7

This example was carried out like example 2 but with a changed molar ratio of acrolein to glycerol of 3 to 1. 99.2 g acrolein/h and 54.5 g glycerol/h are fed in. The reaction product obtained is composed of 45.8% acrolein, 4.7% glycerol, 37.6% acrolein glycerol acetal, 7.5% water and 4.4 % byproducts. Acrolein is reacted to 29.0% with a selectivity of 86.5% and glycerol is reacted to 86.8% with a selectivity of 86.5%.

Example 8

50 g acrolein and 40 g glycerol are placed in a flask. 12 g Amberlyst 15 are added under agitation and the internal temperature adjusted to 15° C. As soon as the mixture is homogeneous, a further 286 g acrolein and 236 g glycerol are uniformly added in drop by drop from two receivers over a period of 1 h so that the reaction mixture remains homogenous. After the end of the addition, the mixture is agitated 30 minutes more, the catalyst filtered off and the mixture compounded with 2 ml of a 1 N Na citrate buffer pH 6. Analysis yields a composition of 30.6% acrolein, 46.9% acrolein glycerol acetal, 10.9% glycerol, 9.2% water and 2.4% byproducts. Acrolein is reacted to 44.1% with a selectivity of 83.5% and glycerol is reacted to 75.9% with a selectivity of 96.6%.

Example 9

This example was carried out like example 8 but with a polymeric organosiloxane containing sulfonate groups (type ASP / Degussa AG) as catalyst:

50 g acrolein and 40 g glycerol are placed in a flask. 12 g polysiloxane ASP ar added under agitation and the internal temperature adjusted to 15° C. As soon as the mixture is homogeneous, a further 286 g acrolein and 236 g glycerol are uniformly added in drop by drop from two receivers over a period of 3 h so that the reaction mixture remains homogenous. After the end of the addition, the mixture is agitated 30 minutes more, the catalyst filtered off and the mixture compounded with 2 ml of a 1 N Na citrate buffer pH 6. Analysis yields a composition of 34.3% acrolein, 39.9% acrolein glycerol acetal, 11.9% glycerol, 9.6% water and 4.3% byproducts. Acrolein is reacted to 37.5% with a selectivity of 83.3% and glycerol is reacted to 73.6% with a selectivity of 85.0%.

Further variations and modifications will be apparent to those skilled in the art from the foregoing and are intended to be encompassed by the claims appended hereto.

German priority application No. P 40 40 362.9 is relied on and incorporated herein.

We claim:

1. A method of producing mixtures of cyclic acrolein glycerol acetals comprising reacting acrolein with glycerol in the presence of a solid acid catalyst to form a reaction mixture, adding acrolein and glycerol to said reaction mixture in such a manner that only one liquid phase is always present, said reaction mixture consisting essentially of acrolein, glycerol, cyclic acrolein glycerol acetal and water, and carrying out the reaction in the presence of said reaction mixture as the sole solvent and, recovering the product of the reaction.

2. The method according to claim 1 wherein said reaction mixture is freed of catalyst and then distilled in the presence of an amount of pH-increasing substance so that said reaction mixture exhibits a pH in a range of 4.5 to 7 in tenfold dilution with water.

3. The method according to claim 1, wherein the reaction is carried out at a temperature in a range of 0° to 50° C.

4. The method according to claim 3 wherein the temperature is 10° to 30° C.

5. The method according to claim 1, wherein a strongly acidic organic or inorganic ion exchanger in the H form is the catalyst.

6. The method according to claim 5 wherein the ion exchanger contains sulfonate groups.

7. The method according to claim 1, wherein a reaction mixture is used as solvent which is obtained from the reaction of acrolein with glycerol in a molar ration of 1.5 to 2.5 and contains 40 to 50% by weight cyclic acrolein glycerol acetals.

8. The method according to claim 2, wherein a buffer solution with a pH in a range of 5 to 7 is used as pH-increasing substance.

9. The method according to claim 8, wherein the pH range is 5.5 to 6.5.

10. The method according to claim 8, wherein the reaction mixture is compounded with such an amount of buffer solution that it exhibits a pH in a range of 5.5 to 7 in tenfold dilution with water.

11. The method according to claim 1, further comprising carrying out the reaction in a continuous manner by dosing acrolein and glycerol in a molar ration of acrolein: glycerol=greater than 1 to 1 to 5 to 1 in a continuous manner into said reaction mixture functioning as solvent, reacting in the presence of said solid acidic catalyst, and continuously removing an amount of said reaction mixture corresponding to the amount dosed in.

12. The method according to claim 11 wherein the ratio is 1.5 to 2.5 to 1.

* * * * *